(12) United States Patent
Trullas Cabanas et al.

(10) Patent No.: US 10,124,044 B2
(45) Date of Patent: Nov. 13, 2018

(54) USE OF PHOTOLYASE FOR REDUCING OR IMPROVING SUBCLINICAL FIELD CANCERIZATION ASSOCIATED WITH ACTINIC KERATOSIS

(75) Inventors: Carlos Ramón Trullas Cabanas, Barcelona (ES); Susana Puig I Sarda, Barcelona (ES); Josep Malvehy Guilera, Barcelona (ES)

(73) Assignees: ISDIN, S.A., Barcelona (ES); HOSPITAL CLINIC BARCELONA, Barcelona (ES); INSTITUT D'INVESTIGACIONS BIOMEDIQUES AUGUST PI I SUNYER, Barcelona (ES)

( * ) Notice: Subject to any disclaimer, the term of this patent is extended or adjusted under 35 U.S.C. 154(b) by 321 days.

(21) Appl. No.: 14/124,873

(22) PCT Filed: Jun. 8, 2012

(86) PCT No.: PCT/EP2012/060852
§ 371 (c)(1),
(2), (4) Date: Mar. 24, 2014

(87) PCT Pub. No.: WO2012/168401
PCT Pub. Date: Dec. 13, 2012

(65) Prior Publication Data
US 2014/0255469 A1    Sep. 11, 2014

Related U.S. Application Data

(60) Provisional application No. 61/502,653, filed on Jun. 29, 2011.

(30) Foreign Application Priority Data

Jun. 9, 2011  (ES) .................................. P201130965
Oct. 21, 2011  (ES) ................................. P201131696

(51) Int. Cl.
*A61K 38/51* (2006.01)
*A61K 9/127* (2006.01)

(52) U.S. Cl.
CPC .............. *A61K 38/51* (2013.01); *A61K 9/127* (2013.01)

(58) Field of Classification Search
None
See application file for complete search history.

(56) References Cited

PUBLICATIONS

Vatve M et al. Management of field change in actinic keratosis. 2007. British Journal of Dermatology. 157, 21-24.*
Kanjilal S et al. p53 mutations in nonmelanoma skin cancer of the head and neck: molecular evidence for field cancerization. 1995. Cancer Research. 55, 3604-3609.*
Ramzi ST et al. An Assessment of the Malignant Potential of Actinic Keratoses and Bowen's Disease: p53 and PCNA Expression Pattern Correlate with the Number of Desmosomes. 2002. The Journal of Dermatology. vol. 29: 562-572.*
Anonymous; "Eryfotona AK-NMSC Crema 50 ML—Prevencion De Diferentes Formas De Cancer Cutaneo, No Melanoma." Farmacia en Casa, Retrieved from the Internet: URL: http://web.archive.org/web/20100611155314/http://www.farmaciaencasaonline.es/eryfotona-aknmsc-crema-p-16524.html [retrieved on Jul. 3, 2012], p. 1.
Camp, William L, et al.; "New Agents for Prevention of Ultraviolet-Induced Nonmelanoma Skin Cancer." Seminars in Cutaneous Medicine and Surgery, 2011, pp. 6-13; vol. 30.
Kraemer, Kenneth H., et al.; "Topical enzyme therapy for skin diseases?" Journal of the American Academy of Dermatology, 2002, pp. 463-466, vol. 46.
Jans, Judith, et al.; "Powerful Skin Cancer Protection by a CPD-Photolyase Transgene."Current Biology, 2005, pp. 105-115, vol. 15.
Stege, Helger, et al.; "Enzyme plus light therapy to repair DNA damage in ultraviolet-B-irradiated human skin." Proceedings of the National Academy of Sciences of the United States of America, 2000, pp. 1790-1795, vol. 97.
International Search Report, dated Jul. 19, 2012.

* cited by examiner

*Primary Examiner* — Paul J Holland
(74) *Attorney, Agent, or Firm* — Tristan A. Fuierer; Moore & Van Allen, PLLC

(57) ABSTRACT

The present invention relates to the use of photolyase enzymes to reduce or improve subclinical skin field cancerization associated with actinic keratosis or non-melanoma skin cancer (NMSC) and methods for the therapeutic treatment of subclinical field cancerization associated with actinic keratosis and/or non-melanoma skin cancer (NMSC).

9 Claims, 1 Drawing Sheet

USE OF PHOTOLYASE FOR REDUCING OR IMPROVING SUBCLINICAL FIELD CANCERIZATION ASSOCIATED WITH ACTINIC KERATOSIS

CROSS-REFERENCE TO RELATED APPLICATIONS

This application is filed under the provisions of 35 U.S.C. § 371 and claims the priority of International Patent Application No. PCT/EP2012/060852 filed on 8 Jun. 2012 entitled "USE OF PHOTOLYASE FOR REDUCING OR IMPROVING SUBCLINICAL FIELD CANCERIZATION ASSOCIATED WITH ACTINIC KERATOSIS" in the name of Carlos Ramón TRULLAS CABANAS, et al., which claims priority to Spanish Patent Application No. P201131696 filed on 21 Oct. 2011, U.S. Provisional Patent Application No. 61/502,653 filed on 29 Jun. 2011 and Spanish Patent Application No. P201130965 filed on 9 Jun. 2011, all of which are hereby incorporated by reference herein in their entirety.

FIELD OF THE INVENTION

The present invention relates to the use of photolyase enzymes to reduce or improve subclinical skin field cancerization associated with actinic keratosis or non-melanoma skin cancer (NMSC) and methods for the therapeutic treatment of subclinical field cancerization associated with actinic keratosis and/or non-melanoma skin cancer (NMSC).

BACKGROUND OF THE INVENTION

Actinic keratosis is defined as a malignant neoplasm of epidermal keratinocytes triggered by exposure to ultraviolet radiation and is an early stage in the continuous process from atypical keratinocyte proliferation to the development of non-melanoma skin cancer (NMSC).

It has been long known that the development of actinic keratosis is associated and frequently preceded by subclinical disorders in the epidermis surrounding or to surround the actinic keratosis lesion. These subclinical disorders make up the so-called subclinical field cancerization. A high probability for developing actinic keratosis lesions and/or squamous cell cancer has been observed in field cancerization (Boudewjin, J. M. et al. 2003. A Genetic Explanation of Slaughter's Concept of Field Cancerization: Evidence and Clinical Implications. Cancer Research 63:1727-1730). Skin field cancerization is the skin area that shares a genetic risk for developing skin carcinoma due to the damage caused by ultraviolet radiation. It includes areas where the actinic keratosis lesion or non-melanoma skin cancer are already present and show cell damage (e.g. cell atypia) or histological damage (e.g. parakeratosis), but also morphologically normal areas that show at the molecular level the same genetic changes induced by ultraviolet light that characterize squamous cell carcinoma of the skin, e.g. mutations or changes in TP53 gene expression (Padilla, R. S. et al. 2010. Gene Expression Patterns of Normal Human Skin Actinic Keratosis, and Squamous Cell Carcinoma. Arch. Dermatol. 146(3):288-293). In this invention we define subclinical field cancerization as the skin area with genetic changes at molecular level (alteration of expression level of proteins such as TP53, p21 or PCNA and decreased expression levels of genes such as PPP1R14A (CPI-17)) induced by ultraviolet light and that does not show clinical evidence of actinic keratosis lesion or non-melanoma skin cancer.

Therefore, there has been an interest in finding therapies that may reduce subclinical field cancerization and, optionally, also existing actinic keratosis lesions and/or non-melanoma skin cancer (NMSC). One of the most common treatments is the topical application of 5% Imiquimod cream. The application of this cream causes an inflammatory response in the field cancerization, while it does not cause this reaction in normal cells, indicating a specific reaction in impaired cells.

On the other hand, the use of photolyase enzymes has been described to repair the DNA damage caused by ultraviolet radiation, more specifically to remove pyrimidine base dimers (CPDs) that are produced when skin is exposed to ultraviolet radiation (Stege, H.2001. Effect of xenogenic repair enzymes on photoimmunology and photocarcinogenesis. Journal of Photochemistry 65:105-108). According to this article, the topical application of photolyase, in addition to removing pyrimidine base dimers, allowed for reducing the immunodepression induced by UVB radiation.

Sun protection creams are also found in the market (ERYFOTONA® AK-NMSC by ISDN, S.A.) that contain photolyase in liposomes, recommended for preventing the occurrence of actinic keratosis and non-melanoma skin cancer.

However, there was no evidence to date that the topical application of photolyase allows for reducing or improving the subclinical skin field cancerization associated with actinic keratosis and/or non-melanoma skin cancer (NMSC).

SUMMARY OF THE INVENTION

The present invention relates to the use of photolyase enzymes to reduce or improve subclinical skin field cancerization associated with actinic keratosis and/or non-melanoma skin cancer (NMSC), to reduce the risk of developing actinic keratosis lesions and/or non-melanoma skin cancer (NMSC) in human patients having a subclinical cancerization field, to methods for the therapeutic treatment of subclinical skin field cancerization associated with actinic keratosis and/or non-melanoma skin cancer (NMSC) and to methods of reducing the risk of developing actinic keratosis lesions and/or non-melanoma skin cancer (NMSC) in human patients having a subclinical cancerization field comprising the topical application on the skin field cancerization of the patient a topical composition comprising photolyase. The present invention also relates to photolyase for use in the topical treatment to reduce or improve the subclinical field cancerization associated with actinic keratosis or non-melanoma skin cancer in a human patient and photolyase for use in the topical treatment to reduce the risk of developing actinic keratosis lesions and/or non-melanoma skin cancer (NMSC) in human patients having a subclinical cancerization field. Treatment methods that reduce subclinical field cancerization are particularly useful for the prevention of actinic keratosis and/or non-melanoma skin cancer (NMSC) in patients who have already shown these diseases, since in these patients the presence of subclinical field cancerization enhances the chances of developing new actinic keratosis lesions and/or non-melanoma skin cancer (NMSC).

DESCRIPTION OF THE INVENTION

Figure 1:
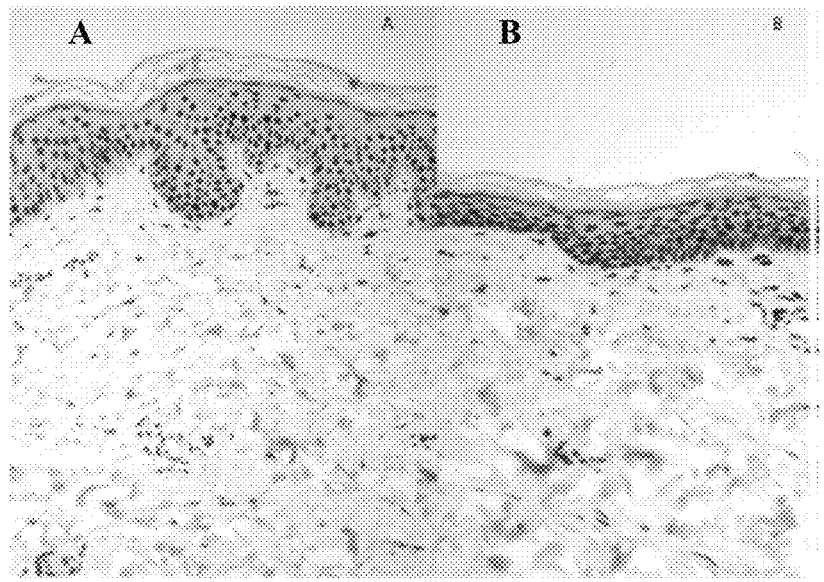
FIG. 1 shows PCNA expression in skin biopsies form a patient before (A) and after 4 weeks (B) of treatment with a topical composition comprising photolyase (amplification × 10).

The inventors have discovered that the topical application of photolyase in human patients allows for both reducing actinic keratosis lesions and/or non-melanoma skin cancer and for reducing or improving the subclinical skin field cancerization associated with these lesions. Improving the field cancerization refers to decreasing the expression level, in epidermal cells which make up the field cancerization, of certain proteins, e.g. TP53, p21 and/or PCNA, and/or increasing the expression levels of CPI-17 (PPP1R14A), which results in a decrease of one or more of the following pathological disorders at the cellular, sub-cellular or molecular level: epidermal hypertrophy, decrease in the epidermal thickness, focal and/or diffuse atypia, parakeratosis, diskeratosis, focal inflammation, which may be assessed by confocal microscopy. Reducing the field cancerization refers to a decrease of the skin area that shows altered expression levels of the above-mentioned biomarkers, in the epidermal cells which make up the field cancerization, particularly increased expression levels of TP53, p21 and/or PCNA, and/or decreased expression levels of CPI-17 (PPP1R14A), with respect to the expression levels in healthy skin. The reduction or improvement of the subclinical skin field cancerization is particularly relevant, since it is known that the probability of developing actinic keratosis and/or non-melanoma skin cancer in such subclinical field cancerization is higher than the probability of these diseases developing in healthy epidermal tissue.

Subclinical skin field cancerization is an area of the epidermis that suffers subclinical disorders frequently caused by exposure to ultraviolet radiation. The filed cancerization usually surrounds the actinic keratosis lesion and/or non-melanoma skin cancer once they have developed but may also precede their development. Clinical diagnosis of actinic keratosis is usually performed by visual inspection of the lesions, optionally together with a dermatoscopic inspection thereof. In this regard, in the present invention clinical signs of actinic keratosis refer to alterations of the skin which can be detected with a naked eye, whereas subclinical alterations are not detectable with the naked eye. In the subclinical field cancerization, cellular and/or tissular alterations are not detectable with a naked eye, although their detection may be accomplished by use of high definition techniques such as dermoscopy, confocal microscopy and/or techniques that require removal of a sample of the tissue to be analyzed. This subclinical skin field cancerization is characterized in that the epidermal cells forming it show altered expression levels of some genes and/or proteins, with respect to the expression levels of said genes and/or proteins in healthy skin tissue (i.e., not showing histopathological alterations), particularly altered expression levels of one or more of the following: TP53, p21, PCNA proteins and CPI-17 (PPP1R14A) gene. These expression levels can be measured, for instance, by real-time reverse transcriptase polymerase chain reaction (RT-PCR), RNA arrays or immunohistochemistry.

CPI-17 (PPP1R14A) gene (UniGene Hs.631569) encodes the regulator subunit (inhibitor) 14A of protein phosphatase 1, (PPP1R14A). TP53 gene is a tumor suppressor gene that encodes the tumor protein p53 (UniGene Hs.654481). p53 is involved in the regulation of growth of keratinocytes, specifically in the control of cell death. Hussein et al. have shown that p53 is involved with the evolution of actinic keratosis lesions as this protein is up-regulated in actinic keratosis as compared to normal skin (Hussein R. et al. 2004. Analysis of p53 and bcl-2 protein expression in the non-tumorigenic, pretumorigenic, and tumorigenic keratinocytic hyperproliferative lesions. Journal of Cutaneous Pathology 31:643-651). p21 is cyclin-dependent kinase inhibitor 1 is a protein that in humans is encoded by the CDKN1A gene (UniGene Hs.370771). p21 mediates p53-induced growth arrest triggered by DNA damage and has been shown to switch off p53 activation to decreased cell proliferation (Lu S. et al. 1999. Expression of cell-cycle proteins p53, p21 (WAF-1), PCNA and Ki-67 in benign, premalignant and malignant skin lesions with implicated HPV involvement. Acta Derm. Venereol. 79:268-273). PCNA is proliferating cell nuclear antigen protein that is encoded by the PCNA gene (UniGene Hs.147433). PCNA has been used as biomarker in the measure of cell proliferation related to the development of actinic keratosis. Besides, an increase in PCNA and p53 expression has been reported in sun-damaged skin with no clinical evidence of AK (Einspahr J. G. et al. 2006. Reproducibility and expression of skin biomarkers in sun-damaged skin and actinic keratoses. Cancer Epidemiology, Biomarkers & Prevention 15:1841-1848).

The inventors have surprisingly found that application of topical compositions comprising photolyase modifies the expression level, in epidermal cells making up the field cancerization, of certain genes, particularly one or more of the following genes: CPI-17 (PPP1R14A), and/or certain proteins, particularly one or more of the following proteins TP53, p21 and PCNA, which is a sign of improvement of the field cancerization. Particularly, application of topical compositions comprising photolyase decreases the expression level of one or more of the following proteins, p21 and PCNA whereas it increases the expression level of CPI-17 (PPP1R14A) gene. A change in the previously mentioned expression levels is a sign of improvement of one or more of the following pathological disorders at the cellular, sub-cellular or molecular level: epidermal hypertrophy, decrease in the epidermal thickness, focal and/or diffuse atypia, parakeratois, diskeratosis, focal inflammation, which may be assessed by confocal microscopy.

Photolyases (EC 4.1.99.3) are DNA repairing enzymes that can excise the pyrimidine dimers formed when DNA is exposed to ultraviolet radiation. In order to perform this excision, the photolyases require exposure to visible light.

Photolyases are available in the market and methods to prepare and purify them are described, for instance, in the book DNA REPAIR: A LABORATORY MANUAL OF RESEARCH PROCEDURES edited by E. Friedberg and P. C. Hanawalt and published by Marcel Dekker, New York, Volume I, Part A and in the European patent application number 0423214A. The product Photosomes® marketed by AGI Dermatics is an example of photolyase-containing liposomes that is available in the market.

One aspect of this invention relates to the use of photolyases for preparing a topical composition to reduce or improve the subclinical skin field cancerization associated with actinic keratosis or non-melanoma skin cancer in a human patient.

Another aspect of this invention relates to the use of photolyases to prepare a topical composition to reduce the risk of developing actinic keratosis lesions and/or non-melanoma skin cancer (NMSC) in human patients having a subclinical cancerization field. In the case of patients who already have actinic keratosis and/or non-melanoma skin cancer (NMSC) the risk of developing new lesions is reduced. Thus, in one embodiment, the present invention relates to any of the previously mentioned uses of photolyases, wherein the patients already have actinic keratosis lesions and/or non-melanoma skin cancer (NMSC) or have experienced these diseases in the past.

Another aspect of this invention relates to a method to reduce or improve subclinical skin field cancerization comprising the topical application on the skin field cancerization of a topical composition comprising photolyase.

Another aspect of this invention relates to a method to reduce the risk of developing actinic keratosis lesions and/or non-melanoma skin cancer (NMSC) in human patients having a subclinical cancerization field comprising topical application in the field cancerization of the patient a topical composition comprising photolyase.

One embodiment of this invention relates to a method to prevent the development of actinic keratosis and NMSC in human patients who had no previous history of AK nor NMSC but suffering of subclinical cancerization in their skin.

In another embodiment, the present invention relates to any of the previously mentioned methods, i.e. method of treatment to reduce or improve the subclinical field cancerization associated with actinic keratosis or non-melanoma skin cancer in a human patient and method of reducing the risk of developing actinic keratosis lesions and/or non-melanoma skin cancer (NMSC) in human patients having a subclinical cancerization field, wherein the patients already have actinic keratosis lesions and/or non-melanoma skin cancer (NMSC) or have experienced these diseases in the past.

Another aspect of this invention relates to photolyase for use in the topical treatment to reduce or improve the subclinical field cancerization associated with actinic keratosis or non-melanoma skin cancer in a human patient.

Another aspect of this invention relates to photolyase for use in the topical treatment to reduce the risk of developing actinic keratosis lesions and/or non-melanoma skin cancer (NMSC) in human patients having a subclinical cancerization field.

In one embodiment, the invention relates photolyase for any of the previously mentioned uses, i.e. in the topical treatment to reduce or improve the subclinical field cancerization associated with actinic keratosis or non-melanoma skin cancer in a human patient and in the topical treatment to reduce the risk of developing actinic keratosis lesions and/or non-melanoma skin cancer (NMSC) in human patients having a subclinical cancerization field, wherein the patients already have actinic keratosis lesions and/or non-melanoma skin cancer (NMSC) or have experienced these diseases in the past.

One embodiment of this invention uses photolyase to prepare a topical composition for reducing or improving the subclinical skin field cancerization and/or reduce the risk of developing actinic keratosis lesions and/or non-melanoma skin cancer (NMSC) in patients suffering Xeroderma Pigmentosum.

Another embodiment of this invention relates to the methods according to the present invention, wherein the patient suffers Xeroderma Pigmentosum.

Another embodiment of this invention relates to photolyases for any of the previously defined used, wherein the patient suffers Xeroderma Pigmentosum.

In other embodiments of this invention the topical composition of photolyase for the uses and/or methods of the present invention comprises photolyase contained in liposomes, preferably in liposomes comprising phospholipids and more preferably in liposomes comprising a mixture of pH-sensitive phospholipids, such as phosphatidylethanolamine and non-pH-sensitive phospholipids, such as phosphatidylcholine and optionally other non-phosphorylated lipids, such as cholesteryl hemisuccinate.

In other embodiments of this invention, the photolyases for the uses and/or methods of the present invention are chosen from photolyases, preferably deazaflavin photolyases obtained from cyanobacteria, preferably from the genus *Anacystis nidulans*. Deazaflavin photolyases are photolyases that, in addition to using FADH⁻ as a cofactor, use 8-hydroxy-7,8-didemethyl-5-deazariboflavin (8-HDF) as an additional cofactor.

In preferred embodiments, the photolyase for the uses and/or methods of the present invention is used as liposomes marketed by AGI Dermatics under the brand name Photosomes®.

In other embodiments of this invention the topical composition of photolyase for the uses and/or methods of the present invention also comprises UV filters.

Example

Subjects and Methods

Design

Pilot, prospective, controlled, intervention clinical study to evaluate the effect of a topical composition comprising photolyase (Eryfotona® AK-NMSC, commercially available in Spain) in the treatment of the field cancerization. The evaluation was performed subclinically during the treatment, by reflectance confocal microscopy (RCM), and at the beginning and at the end of the treatment by histopathology and immunohistochemistry assessment. RCM allows non-invasive monitoring of treatment response in vivo and permits early detection of cellular damages.

Subjects

Eleven patients older than 50 years old and 2 xeroderma pigmentosum patients, affected by AK lesions in a sun exposed area, were included. The study was carried out treating skin areas devoid of AK lesions as determined by clinical signs. The patients consented to participate in the trial after reading and understanding the information approved by the ethical committee, and the study was conducted according to the Declaration of Helsinki Principles.

Methods and Statistical Analyses

The conduct of this study was approved by the IRB of the investigative centre and the patients gave their written, informed consent. The area treated was documented with RCM (Vivascope 1500, Lucid Corp) (0.8×0.8 cm) to cover the area to be studied. Two 3-mm punch biopsies were performed in two of the representative areas and documented with images. The studied product (topical composition comprising photolyase (Eryfotona® AK-NMSC) or a sunscreen with UV filters but without the enzyme photolyase, both products with an identical sun protection factor) was applied in the area of treatment for 4 weeks, in the morning and 4-6 hours later. At the end of the treatment (week 4), a final evaluation was performed and 2 punch biopsies obtained in 2 representative areas previously not damaged with the biopsies performed at patient inclusion. Nine patients were treated with the study product and three patients received the sunscreen cream. One patient refused to apply the treatment after the inclusion, and withdrew from the study.

Evaluation of the Confocal Microscopy

The following previously described RCM criteria (Aghassi et al. (2000), J Am Acad Dermatol 43: 42-48; Ulrich et al. (2007), Br J Dermatol 156: 13-17; Ulrich et al. (2007), *Br J Dermatol* 156: 47-52; Ulrich et al. (2008), Dermatol Surg 34: 610-619; and Scope et al. (2007), J Am Acad Dermatol 57: 644-658) were assessed in this study (Table 1): 1) Three RCM features were evaluated at the stratum corneum level: presence of scaling, presence of detached corneocytes and presence of polygonal nucleated cells. 2) Three RCM features were evaluated at the spinous-granulous layer: presence of atypical honeycomb pattern, presence of disarranged epidermal pattern and presence of round nucleated cells, and 3) Two RCM criteria were considered at the Dermis: presence of round blood vessels traversing dermal papilla and presence of inflammatory cells.

A Total RCM Score was calculated with the mean of all the previous scores.

Evaluation of the Immunohistochemistry

Immunohistochemical studies for p21 and PCNA were performed from punch biopsies fixed with formalin and embedded in paraffin with the automated immunohistochemical system Bond Max (Menarini). The primary antibodies used in the study were p21 leica (dilution 1/40) and PCNA leica dilution 1/50.

The statistical analysis for qualitative assessment was performed with a Chi2 corrected with Fisher test in (2×2 tables) when required by sample size. For quantitative variables, we compared the mean score for each parameter before the treatment with the mean score for each parameter at the end of the study. Student t test was used for paired samples with normally distributed variables, and the ANOVA test was used for multiple comparisons.

RNA Extraction

Punch biopsies were embedded in RNAlater (Quiagen, US) and stored at −80° C. Total RNA isolation was conducted using Trizol (Invitrogen Life Technologies, Carlsbad, Calif.) extraction based methods as indicated in the manufacturer's protocol, followed by purification in commercial columns (Quiagen, Valencia, Calif.). Briefly, disruption and homogenization of skin samples was performed using Polytron System PT1200E (Kinematica, Switzerland) homogenized and lysed in Trizol. After chloroform addition, RNA was isolated from the aqueous phase. RNA was precipitated with isopropanol, washed with 70% ethanol, and redissolved in RNase-free buffer. Total isolated RNA was further purified using an RNeasy kit (Quiagen, Valencia, Calif.). RNA concentration was determined using a NanoDrop Spectrophotometer (Thermo Scientific) and integrity of the RNA was verified by Bioanalyzer 2100 (Agilent, US). The RNA integrity number was in all cases higher than 7.9.

Taqman Real-Time Reverse Transcriptase Polymerase Chain Reaction (RT-PCR)

cDNA was reverse transcribed from total RNA using Taqman PCR Core Reagment kit (Roche Applied Science, Penzbergf, Germany). RT-PCR was performed using Taqman Universal PCR master Mix (Roche Applied Science, Penzbergf, Germany). The reaction was performed in a ABI 7900HT sequence detection instrument (Applied Biosystems, CA, US). Taqman gene-specific primers and probes for selected genes (CPI-17 and WDR72) were purchased from Applied Biosystems. The GADPH gene was used to normalize each sample. RNA from normal skin was used as calibrator. Quantitative PCR was evaluated using the relative quantification method of $\Delta\Delta Ct$ [Livak K J and Schmitgen T D (2001), *Methods* 25: 402-408]. Expression values were evaluated by t-test for equality means using the SPSS 17.0 software.

Results

Thirteen patients (12 males and 1 female; 2 of them affected by xeroderma pigmentosum; mean age 72 y.o.) have been included; one patient refused the treatment after the first evaluation and before the first biopsy. Two patients refused the second biopsy due to concomitant personal issues. Subclinical assessment, confocal microscopy and histopathology evaluation after treatment demonstrate an improvement in the field cancerization after treatment with the topical composition comprising photolyase (Eryfotona® AK-NMSC). In contrast, this improvement is not present in the 3 patients treated with the sunscreen.

The results of the evaluation of the RCM are summarized in Table 1. The presence of scaling, detached corneocytes and polygonal nucleated cells in the stratum corneum decreased during the treatment with the topical composition comprising photolyase (Eryfotona® AK-NMSC) ($p=0.004$, $p=0.018$ and $p=0.021$, respectively). We also noted an improvement of the atypical honeycomb pattern and round nucleated cells at the spinous granulous layer ($p<0.0005$ and $p=0.019$, respectively). Finally, the mean RCM score improved significantly ($p=0.002$) in the patients receiving topical application of the topical composition comprising photolyase (Eryfotona® AK-NMSC).

TABLE 1

Evolution of RCM scores in patients receiving treatment of the field cancerization with a topical composition comprising photolyase (Eryfotona ® AK-NMSC). The values represent the mean and the standard deviation is shown in parentheses. $t_0$ is the initial time prior to treatment, $t_f$ is the final time at the end of the 4-week treatment period and CI is the confidence interval.

|  | $t_0$ | $t_f$ | Change | 95% CI | P value |
|---|---|---|---|---|---|
| Scaling | 1.18 (0.7) | 0.25 (0.3) | −0.93 (0.5) | −1.423 to −0.434 | 0.004 |
| Corneocytes | 1 (0.9) | 0.18 (0.4) | −0.82 (0.7) | −1.443 to −0.199 | 0.018 |
| Polygonal nucleated cells stratum corneum | 0.69 (0.5) | 0.14 (0.2) | −0.55 (0.5) | −0.977 to −0.117 | 0.021 |
| Atypical honey comb | 1.39 (0.4) | 0.43 (0.4) | −0.96 (0.1) | −1.052 to −0.877 | <0.0005 |
| Disarranged epidermal pattern | 0.15 (0.2) | 0 | −0.15 (0.2) | −0.345 to −0.036 | 0.095 |

TABLE 1-continued

Evolution of RCM scores in patients receiving treatment of the field cancerization with a topical composition comprising photolyase (Eryfotona ® AK-NMSC). The values represent the mean and the standard deviation is shown in parentheses. $t_0$ is the initial time prior to treatment, $t_f$ is the final time at the end of the 4-week treatment period and CI is the confidence interval.

|  | $t_0$ | $t_f$ | Change | 95% CI | P value |
|---|---|---|---|---|---|
| Round nucleated cells at spinous granulous layer | 0.98 (0.7) | 0.42 (0.4) | −0.56 (0.5) | −0.993 to −0.127 | 0.019 |
| Round blood vessels traversing dermal papilla | 0.12 (0.2) | 0.04 (0.1) | −0.08 (0.2) | −0.314 to −0.148 | 0.413 |
| Inflammatory cells | 0.49 (0.6) | 0.32 (0.4) | −0.17 (0.3) | −0.463 to −0.131 | 0.221 |

Immunohistochemistry results are summarized in table 2. Interestingly, after 4 weeks of treatment of the field cancerization with the topical composition comprising photolyase (Eryfotona® AK-NMSC), p21 expression in suprabasal layers decreased, (p=0.042) and a tendency to a decreased PCNA expression in the basal layer was also detected (p=0.076).

TABLE 2

Immunohistochemistry scores before ($t_0$) and after 4-week treatment ($t_f$) with a topical composition comprising photolyase (Eryfotona ® AK-NMSC) in the field cancerization. N is the number of patients, SD is the standard deviation.

|  |  | Mean | N | SD | P value |
|---|---|---|---|---|---|
| PCNA basal | $t_0$ | 2.67 | 6 | 0.516 | 0.076 |
|  | $t_f$ | 2.17 | 6 | 0.408 |  |
| PCNA suprabasal | $t_0$ | 2.83 | 6 | 0.408 | 0.296 |
|  | $t_f$ | 2.33 | 6 | 0.816 |  |
| p21 basal | $t_0$ | 0.5 | 6 | 0.548 | 0.363 |
|  | $t_f$ | 0.17 | 6 | 0.408 |  |
| p21 suprabasal | $t_0$ | 2.17 | 6 | 0.408 | 0.042 |
|  | $t_f$ | 1.33 | 6 | 0.816 |  |

Figure 2:
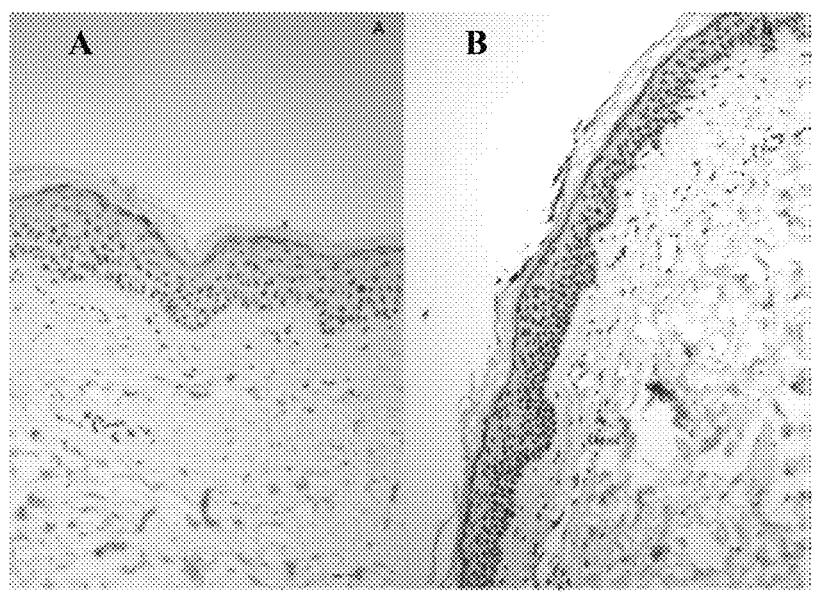
FIG. 2 shows p21 expression in skin biopsies form a patient before (A) and after 4 weeks (B) of treatment with a topical composition comprising photolyase (amplification × 10).

Immunohistochemical studies in skin biopsies from a patient before and after 4 weeks of treatment with the topical composition comprising photolyase (Eryfotona® AK-NMSC) show a decrease in the PCNA expression at the basal layer (FIG. 1) and a decrease in p21 expression at upper stratus of the epidermis (FIG. 2). Expression of CPI-17 was evaluated in the field cancerization of seven patients by quantitative RT-PCR before and after 4 weeks of treatment with the topical composition comprising photolyase (Eryfotona® AK-NMSC) (Table 3). An increase in CPI-17 expression was noted after the treatment with the topical composition comprising photolyase.

TABLE 3

Fold change of genomic expression of CPI-17 gene in the field cancerization of 7 patients following 4-week treatment with the topical composition comprising photolyase (Eryfotona ® AK-NMSC).

| Patient | CPI-17 |
|---|---|
| 1 | 2.98 |
| 2 | 6.51 |
| 3 | 1.82 |
| 4 | 0.99 |
| 5 | 2.11 |
| 6 | 0.89 |
| 7 | 1.12 |
| Mean | 2.35 |

The invention claimed is:

1. A method of treatment of a subclinical cancerization skin field to reduce the risk of developing actinic keratosis lesions and/or non-melanoma skin cancer (NMSC) in human patients, said method comprising applying a topical composition comprising photolyase on a subclinical cancerization skin field of the patient, wherein the subclinical cancerization skin field is characterized by increased expression levels of p21 and/or PCNA, and/or decreased expression levels of CPI-17 with respect to the expression levels in healthy skin, and wherein the topical composition comprising photolyase is applied for at least 4 weeks, and wherein the reduction in the risk of developing actinic keratosis lesions and/or NMSC in human patients is achieved by one or more of the following: decrease of the scaling, decrease of detached corneocytes, decrease of polygonal nucleated cells in the stratum corneum, improvement of the atypical honeycomb pattern, and/or improvement of round nucleated cells at spinous granulous layer.

2. The method according to claim 1 wherein the patients already have actinic keratosis lesions and/or non-melanoma skin cancer (NMSC) or have experienced these diseases in the past.

3. The method according to claim 1, wherein the patient suffers Xeroderma Pigmentosum.

4. The method according to claim 1, wherein the composition contains photolyase incorporated into liposomes.

5. The method according to claim 4, wherein liposomes comprise phospholipids.

6. The method according to claim 1, wherein the photolyase is a deazaflavin photolyase.

7. The method according to claim 1, wherein the photolyase is obtained from cyanobacteria.

8. The method according to claim 7, wherein the cyanobacteria are from the genus *Anacystis nidulans*.

9. The method according to claim 1, wherein the topical composition also comprises UV filters.

* * * * *